US012748042B2

(12) United States Patent
Kusters

(10) Patent No.: US 12,748,042 B2
(45) Date of Patent: Sep. 29, 2026

(54) OPTICAL SYSTEMS AND METHODS FOR GRADING PLASMA DURING WHOLE BLOOD SEPARATION

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 92 days.

(21) Appl. No.: 18/356,121

(22) Filed: Jul. 20, 2023

(65) Prior Publication Data

US 2024/0027333 A1 Jan. 25, 2024

Related U.S. Application Data

(60) Provisional application No. 63/391,167, filed on Jul. 21, 2022.

(51) Int. Cl.
*G01N 21/31* (2006.01)
*G01N 1/40* (2006.01)
*G01N 33/49* (2006.01)

(52) U.S. Cl.
CPC ........... *G01N 21/31* (2013.01); *G01N 1/4077* (2013.01); *G01N 33/491* (2013.01); *G01N 2001/4083* (2013.01); *G01N 2201/08* (2013.01)

(58) Field of Classification Search
CPC ............. G01N 33/491; G01N 33/5002; G01N 1/4077; G01N 21/31; G01N 21/251
See application file for complete search history.

(56) References Cited

U.S. PATENT DOCUMENTS

| | | | | |
|---|---|---|---|---|
| 9,547,899 | B1 * | 1/2017 | Pyayt | G01N 33/491 |
| 10,893,829 | B2 | 1/2021 | Kusters et al. | |
| 2020/0166451 | A1 | 5/2020 | Kusters et al. | |

FOREIGN PATENT DOCUMENTS

| | | | | |
|---|---|---|---|---|
| EP | 3741460 | A1 | 11/2020 | |
| JP | 2009085824 | A | 4/2009 | |
| WO | 9838961 | A1 | 9/1998 | |
| WO | WO-2020240015 | A2 * | 12/2020 | G01N 15/0205 |
| WO | 2021194824 | A1 | 9/2021 | |

OTHER PUBLICATIONS

Rodriguez, “A spectroscopic method of determining color of petroleum products using CIELab color space with LED illumination”, 2017 (Year: 2017).*
Jennifer D. T. Kruschwitz, “Specialized Color Targets for Spectral Reflectance Reconstruction of Magnified Images”, 2015. (Year: 2015).*
Yi Wang, “Smartphone spectrometer for colorimetric biosensing”, 2015 (Year: 2015).*
European Search Report and Written Opinion issued in connection with counterpart EP Application No. 23186699, dated Dec. 21, 2023.

* cited by examiner

*Primary Examiner* — Maurice C Smith
(74) *Attorney, Agent, or Firm* — Cook Alex Ltd.

(57) ABSTRACT

An optical plasma grading system includes a broadband light source configured to emit light having wavelengths in a visible spectrum, an optical spectrometer configured to receive a reflected portion of the emitted light and analyze at least a portion of the received, reflected light to determine a main wavelength of the portion of the received reflected light, and a controller operably connected to the optical spectrometer, the controller configured to determine a plasma grade of the plasma based at least upon the main wavelength of the plasma.

18 Claims, 10 Drawing Sheets

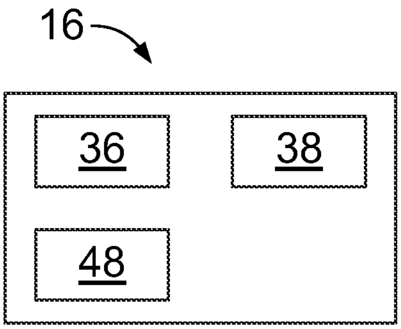
FIG. 6
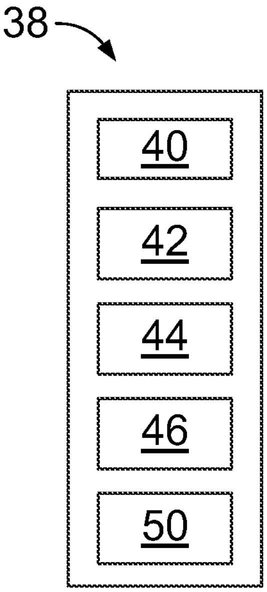
FIG. 7
44 46
| Wavelength Information | Grade Information |
|---|---|
| Visible Color Stored Wavelength / Wavelength Range | Stored Plasma Grade |
| $\lambda_1$ | $PG_1$ |
| $\lambda_2$ | $PG_2$ |
| $\lambda_3$ | $PG_3$ |
FIG. 8

OPTICAL SYSTEMS AND METHODS FOR GRADING PLASMA DURING WHOLE BLOOD SEPARATION

CROSS-REFERENCE TO RELATED APPLICATIONS

This application claims the benefit of and priority to U.S. Provisional Patent Application Ser. No. 63/391,167 filed on Jul. 21, 2022, the contents of which are incorporated by reference herein.

BACKGROUND

Field of the Disclosure

The present disclosure relates to systems and methods for automated plasma grading in a whole blood separation process based on the color of the plasma. More particularly, the present disclosure relates to systems and methods for determining a main wavelength of light reflected by plasma and grading the plasma according to the main wavelength.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, III., which is an affiliate of Fresenius Kabi AG of Bad Homburg, Germany, or other centrifugal separation devices, or a spinning membrane-type separator, such as the AUTOPHERESIS-C® and AURORA® devices from Fenwal, Inc.

In a whole blood manufacturing setting, plasma is graded based on visual appearance, and the plasma grade determines how the plasma will be used, i.e., for fractionation, transfusion, cryoprecipitate, or disposal. Common grades for plasma include, but are not limited to, clear yellow plasma, red-tinted clear plasma, yellow lipemic plasma, red-tinted lipemic plasma and green plasma. In current practice, plasma units are graded manually by comparing the visual plasma color to a pre-established color grading system, often provided in printed form, e.g., on a poster or card at the grading station. However, such a grading process is labor and resource intensive, and may be subject to inconsistent or subjective grading.

Some blood processing systems may include an optical device for monitoring the composition of the blood or a component of the blood. A common approach to non-invasive blood and blood constituent analysis is based on the amount of light transmitted through the fluid. For example, U.S. Pat. No. 10,893,829 (which is incorporated herein by reference) describes an optical system and method for measuring free hemoglobin, i.e., for quantifying free hemoglobin levels. While such a quantitative analysis may produce reliable results with respect to measuring free hemoglobin, it would be desirable to provide systems and methods for grading plasma.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method for grading blood plasma includes emitting, from a broadband light source, light having wavelengths in a visible range and directing the emitted light to a vessel at an incidence angle. The method also includes receiving, at an optical spectrometer, a reflected light portion of the emitted light and analyzing, with the optical spectrometer, at least a portion of the received reflected light to determine a main wavelength of the received reflected light. The method further includes determining, with a controller, the plasma grade of the plasma using the main wavelength.

In another aspect, an optical plasma grading system includes a broadband light source configured to emit light having wavelengths in a visible spectrum, an optical spectrometer configured to receive a reflected portion of the emitted light and analyze at least a portion of the received, reflected light to determine a main wavelength of the portion of the received reflected light, and a controller operably connected to the optical spectrometer. The controller is configured to determine a plasma grade of the plasma based on the main wavelength of the plasma.

In still another aspect, a blood processing and/or manufacturing system includes a processing device having pump system, a valve system, a centrifuge and a nesting module. The system also includes a fluid flow circuit having a plurality of fluid containers, a flow control cassette, and a separation chamber interconnected with one another with a plurality of fluid conduits. The flow control cassette is removably connected to the processing device at the nesting module and interfaces with one or more pumps of the pump system and one or more valves of the valve system. The separation chamber is received in the centrifuge. The pump system, valve system, and centrifuge are selectively operable to provide a flow path through which whole blood flows into the separation chamber, is separated by the centrifuge into plasma and red blood cell components, and the plasma flows to a plasma container of the plurality of fluid containers. The system further includes a broadband light source configured to emit light having wavelengths in a visible spectrum. The emitted light is directed onto a surface of a fluid vessel of the one or more fluid vessels or onto a surface of the plasma container. At least a portion of the emitted light is transmitted through the fluid vessel or the plasma container, and a portion of the transmitted light is reflected by the plasma within the fluid vessel or the fluid container. An optical spectrometer is configured to receive at least a portion of the light reflected by the plasma and analyze at least a portion of the received, reflected light to determine a main wavelength of the portion of the received reflected light. A controller is operably connected to the optical spectrometer. The controller is configured to determine a plasma grade of the plasma based on the main wavelength of the plasma.

These and other aspects of the present subject matter are set forth in the following detailed description of the accompanying drawings.

BRIEF DESCRIPTION OF THE DRAWINGS

FIG. 6 is block diagram of a controller of the optical plasma grading system of FIG. 1 according to examples of the present disclosure;

FIG. 7 is a block diagram of a memory of the controller of FIG. 6 according to examples of the present disclosure;

FIG. 8 is a table showing associations between wavelength information and grade information stored in the memory of FIGS. 6 and 7, according to examples of the present disclosure;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

An optical plasma grading system 10 according to various examples described herein is configured to determine a grade for blood plasma based on the color of the plasma. To this end, the optical plasma grading system 10 is configured to direct emitted light onto plasma, such that a portion of the light is reflected from the plasma. The optical plasma grading system 10 is further configured to receive a portion of the reflected light and analyze the reflected light to determine a main wavelength of light reflected from the plasma. The main wavelength substantially corresponds to a visible color of the plasma. The optical grading system 10 may determine a plasma grade for the plasma 22 based, at least in part, on the main wavelength of the plasma 22.

Figure 1:
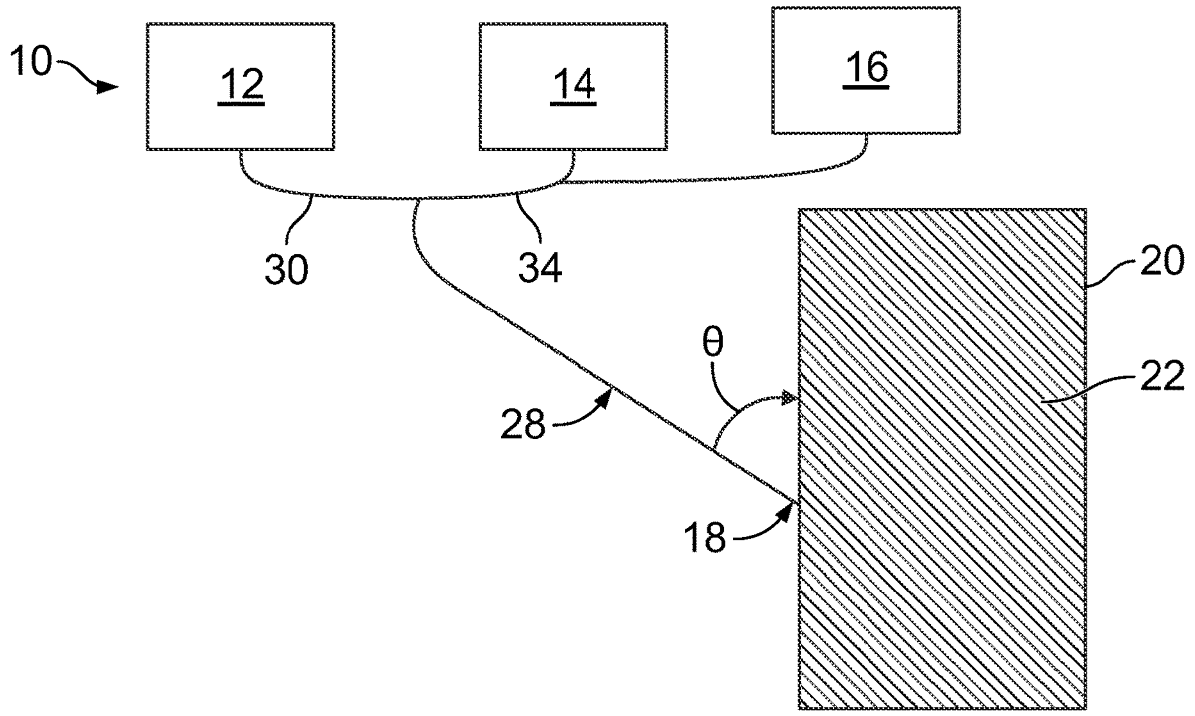
FIG. 1 is a diagram of an optical plasma grading system according to examples of present disclosure.

Referring now to FIG. 1, an optical plasma grading system 10 according to embodiments herein includes a broadband light source 12, an optical spectrometer 14 and a controller 16. The broadband light source 12 is configured to emit a light 18 having wavelengths in the visible range. In one example, the broadband light source 12 emits light 18 including at least all wavelengths in the visible range (from approximately 400 nm to approximately 700 nm). The broadband light source 12 may also emit light having wavelengths above and/or below the visible range. An example of a suitable broadband light source 12 includes a stabilized tungsten-halogen light source configured to emit a light 18 having all wavelengths between 360 nm and 2600 nm of the type marketed by Thorlabs, Inc. of Newton, New Jersey. It will be appreciated, however, that the broadband light source 12 may also be differently configured without departing from the scope of the present disclosure.

Figure 2:
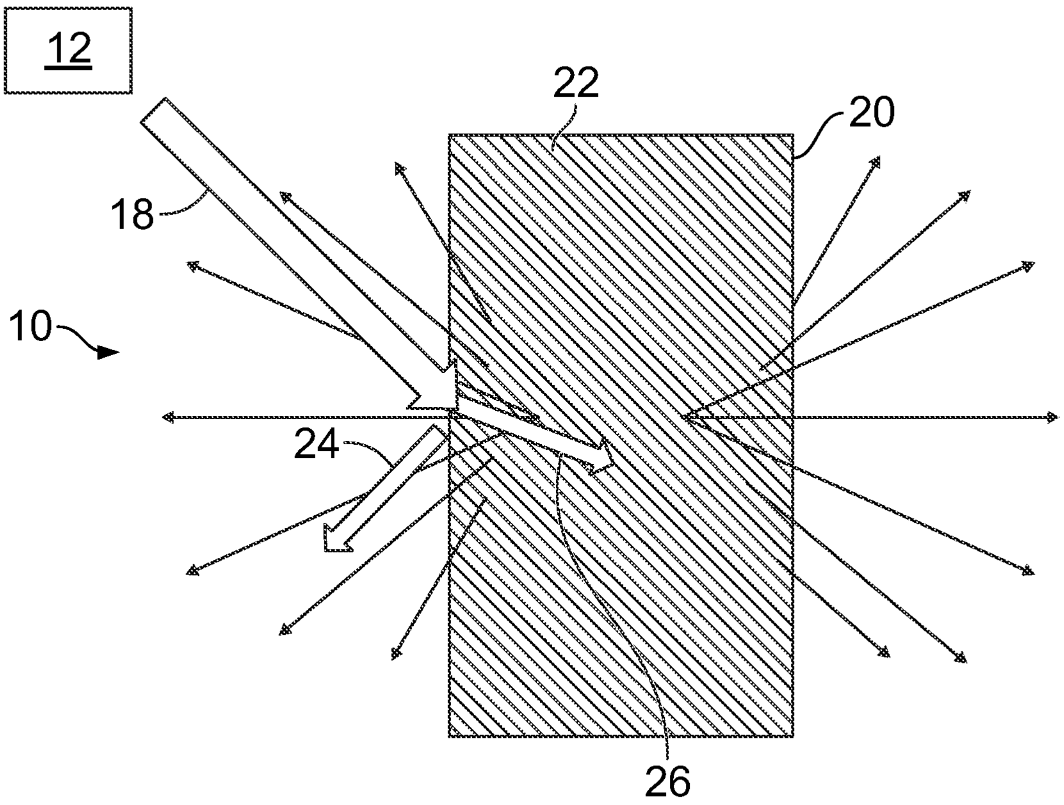
FIG. 2 is a partial diagram of the optical plasma grading system of FIG. 1 further showing emitted light entering a vessel.

The broadband light source 12 is oriented to emit light 18 toward a vessel 20 having plasma 22 arranged therein. With reference to FIG. 2, the light 18 may be emitted by the broadband light source 12 and interact with the vessel 20 such that a first portion 24 of the light 18 is reflected off a surface of the vessel 20 (specular reflection), while a second portion 26 of the light 18 is transmitted through the surface of the vessel 20 and into the vessel 20. As described further below, the vessel 20 may be, for example, a fluid conduit containing plasma and/or a fluid container in which plasma is collected.

Referring again to FIG. 1, the light 18 may be directed to strike the surface of the vessel 20 at an incidence angle $\theta$. The incidence angle $\theta$ may be selected to reduce the degree of specular reflection. For example, at an angle of 90 degrees (i.e., normal to the vessel surface), there will tend to be a significant amount of specular reflection. On the other hand, if the angle $\theta$ is 0 degrees, then the plasma 22 will not be exposed to the light 18. In the present embodiments, it has been found that an incidence angle $\theta$ in the range of 30 degrees to 60 degrees may be advantageous for reducing the degree of specular reflection and producing more sensitive measurements. In one example, the angle $\theta$ is approximately 45 degrees.

The broadband light source 12 may be oriented to direct the light 18 at the angle $\theta$ with respect to the surface of the vessel 20. Alternatively, and with reference to FIGS. 1 and 3, the optical plasma grading system 10 may further include an optical fiber bundle 28 operably connected to the broadband light source 12. The optical fiber bundle 28 may include at last one optical transmission fiber 30 configured to pass at least a portion of the emitted light 18 from broadband light source 12 to vessel 20, and further, may direct the at least a portion of the light 18 onto the vessel 20 at the selected incidence angle $\theta$.

In one embodiment, optical fiber bundle 28 includes a plurality of optical transmission fibers 30. For example, the optical fiber bundle 28 may include six optical transmission fibers 30. However, it will be appreciated that the illustrated configuration of the optical fiber bundle 28 is presented for the purposes of example only, and that other configurations may also be employed. For example, in other embodiments, the optical fiber bundle 28 may include more optical transmission fibers 30 or fewer optical transmission fibers 30. In one example, the optical fiber bundle 28 may include only a single optical transmission fiber 30.

Figure 4:
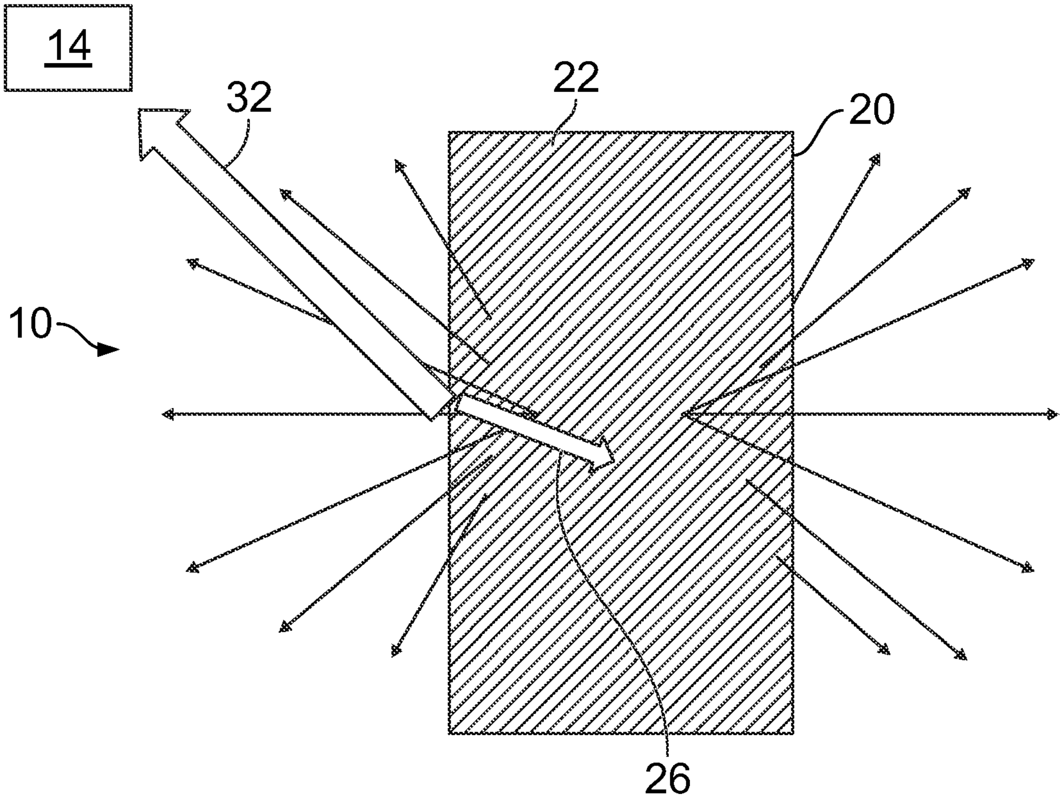
FIG. 4 is a partial diagram of the optical plasma grading system of FIG. 1 further showing light reflected by the plasma.

With reference to FIGS. 2 and 4, when light 18 emitted from the broadband light source 12 strikes the surface of the vessel 20, the first portion 24 of the light 18 is reflected as specular reflection and the second portion 26 of the light 18 is transmitted through the surface of the vessel 20 and into vessel 20 (i.e., to the plasma 22) at an angle according to Snell's Law. A portion 32 of the transmitted (i.e., second) portion 26 of the light 18 is reflected back out of the vessel 20 by the plasma 22 for receipt by the optical spectrometer 14. This reflected portion 32 of the transmitted portion 26 of the light 18 may be referred to herein as the plasma reflected light 32.

Figure 5:
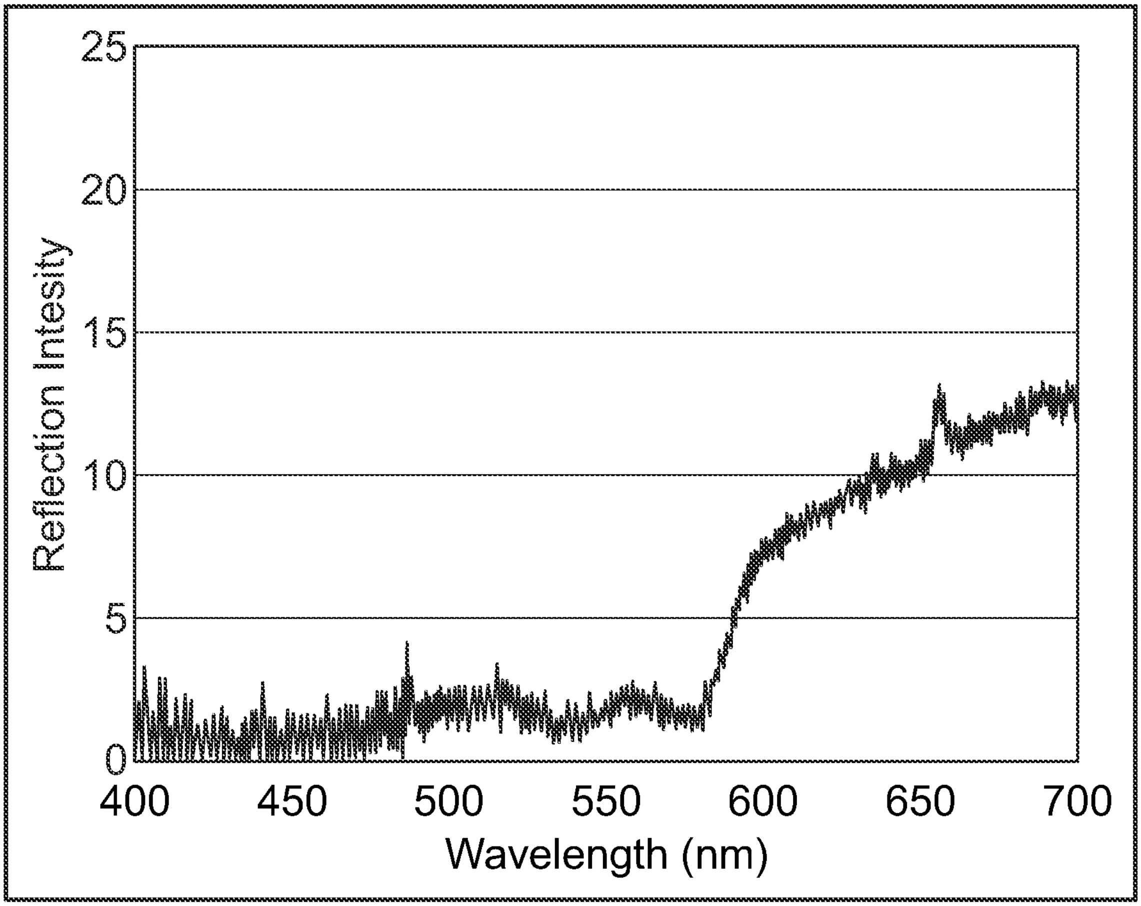
FIG. 5 is a chart showing an example of an optical spectrum produced by an optical spectrometer for determining a main wavelength of light reflected by the plasma.

The optical spectrometer 14 is configured to analyze at least a portion of the received plasma reflected light 32. In one example, the optical spectrometer 14 is configured to analyze the received plasma reflected light by measuring and differentiating the wavelengths contained in the at least a portion of the received plasma reflected light 32 to produce an optical spectrum of the plasma reflected light 32. As shown in the example of FIG. 5, an intensity of the plasma reflected light 32 at the different wavelengths may be determined from the optical spectrum of the plasma reflected light 32. The optical spectrometer 14 is further configured to determine a main wavelength, also referred to in the art as a dominant wavelength, associated with the plasma 22 from the optical spectrum in a known manner, for example, by using a conventional color specification system, which may be software of the type marketed by Thorlabs, Inc. An example of a suitable optical spectrometer 14 includes a compact CCD spectrometer capable of measuring the intensity of light at each wavelength in the range of 200 nm-1000 nm of the type marketed by Thorlabs, Inc., but may also be differently configured without departing from the scope of the present disclosure.

Figure 3:
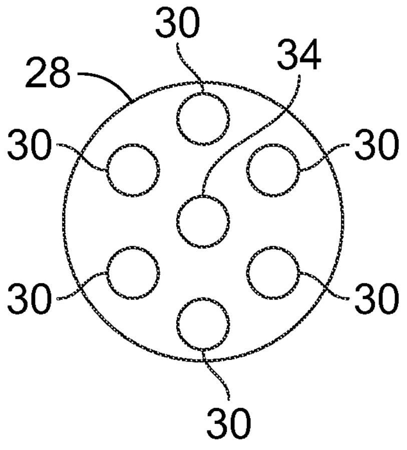
FIG. 3 is an end-view diagram showing an optical fiber bundle according to examples of the present disclosure.

As shown in FIGS. 1 and 3, the optical fiber bundle 28 may also be operably coupled to the optical spectrometer 14 and include at least one optical reception fiber 34. The at least one optical reception fiber 34 is configured to receive at least a portion of the plasma reflected light 32 and pass the received plasma reflected light 32 to the optical spectrometer 14.

In one example, as shown in FIG. 3, the optical reception fiber 34 may be centrally arranged relative to the plurality of the optical transmission fibers 30, at least at an end of the optical fiber bundle 28 from which the light 18 is directed to the vessel 20 and plasma reflected light 32 is received. An example of a suitable optical fiber bundle 22 includes a Thorlabs 200 um Fiber Bundle Reflection Probe marketed by Thorlabs, Inc. It will be appreciated, however, the optical fiber bundle 28 may also be differently configured without departing from the scope of the present disclosure.

The controller 16 is configured to determine a plasma grade for the plasma 22 based at least on the main wavelength. The controller 16 may be variously configured without departing from the scope of the present disclosure. In one embodiment, and with reference to FIGS. 6 and 7, the controller 16 may include a microprocessor 36, which may include multiple physical and/or virtual processors. The controller 16 may include one or more electrical circuits designed to carry out the actions described herein. For example, the controller 16 may include a microprocessor and other circuits or circuitry. In addition, the controller 16 may include one or more memories 38. Instructions 40 by which the microprocessor 36 is programmed may be stored on the memory 38 associated with the microprocessor 36, which memory/memories 38 may include one or more tangible non-transitory computer readable memories, having computer executable instructions stored thereon, which when executed by the microprocessor 36, may cause the microprocessor 36 to carry out one or more actions as described herein.

It will be appreciated, that in general, light emitted onto a vessel and into a fluid sample may be transmitted through the fluid sample typically scattering as it propagates (diffuse transmission), absorbed by the fluid sample, and/or reflected (i.e., diffuse reflectance) by the fluid sample. A fluid without cellular content, such as the plasma, typically exhibits relatively low scattering, for example, as compared to whole blood and blood components, which are turbid media. Such blood and blood components typically exhibit low to moderate absorption and strong scattering properties. Accordingly, the plasma 22 of the present embodiments may exhibit relatively low scattering.

Referring again to FIG. 7, the controller 16 may store, for example in a memory 38 of the one or more memories, plasma grading information 42. As shown in FIGS. 7 and 8, the plasma grading information 42 may include wavelength information 44 which includes a plurality of stored wavelengths and/or wavelength ranges ($\lambda_1$, $\lambda_2$, $\lambda_3$ . . . ) and grade information 46 which includes a plurality of stored plasma grades ($PG_1$, $PG_2$, $PG_3$ . . . ). The stored wavelengths or wavelength ranges may generally correspond to visible colors upon which plasma grades may be manually assigned in conventional processes. That is, the stored wavelengths or wavelength ranges may generally correspond to different visible colors associated with respective plasma grades which may be found, for example, on conventional plasma grading charts or cards. Each stored wavelength or wavelength range of the wavelength information 44 is associated with a stored plasma grade of the grade information 46. In one example, the plasma grading information 42 may be provided as a table having the stored wavelengths or wavelengths ranges of the wavelength information 44 associated with corresponding stored plasma grades of the grade information 46, as shown in FIG. 8. It will be appreciated however, that the plasma grading information 42 may be stored in a variety of suitable formats and is not limited to the example above. For instance, the wavelength information 44 may include stored information in addition to or derived from the stored wavelengths or wavelength ranges referenced above.

The controller 16 is configured to determine a grade of the plasma 22 based on the main wavelength and the plasma grading information 42. For example, the controller 16 may compare the main wavelength associated with the plasma 22 to the plurality of stored wavelengths or wavelength ranges (e.g., $\lambda_1$, $\lambda_2$, $\lambda_3$ . . . ) of the wavelength information 44 and identify a stored wavelength or wavelength range which corresponds to the main wavelength. That is, the controller 16 may identify a stored wavelength that is equal to the main wavelength (within tolerances) and/or a stored wavelength range within the which the main wavelength is contained. The controller 16 may determine the plasma grade of plasma 22 to be the stored plasma grade associated with the identified stored wavelength or wavelength corresponding to the main wavelength. For instance, where the main wavelength $\lambda_{main}$ is equal to a stored wavelength $\lambda_2$, the controller 16 may determine the plasma grade for plasma 22 to be the stored plasma grade $PG_2$ associated with the stored wavelength $\lambda_2$.

The controller 16 may also be configured to generate an output indicative the determined plasma grade for the plasma 22. In some examples, the controller 16 may include, or be operably connected to, a user interface device 48, such as a touchscreen display. The output may be provided to a user via the user interface device 48. In some examples, the controller 16 may be integrated with the optical spectrometer 14. In other examples, the controller 16 may be connected to the optical spectrometer 14 and configured to communicate with the optical spectrometer 14 such that various information may be exchanged between the optical spectrometer 14 and the controller 16 and/or may be transmitted from the optical spectrometer 14 to the controller 16 or vice versa. In other examples, the controller 16 and/or the user interface device 48 may be provided as part of a separate device or system with which the optical spectrometer 14 may operate in combination.

Figure 9:
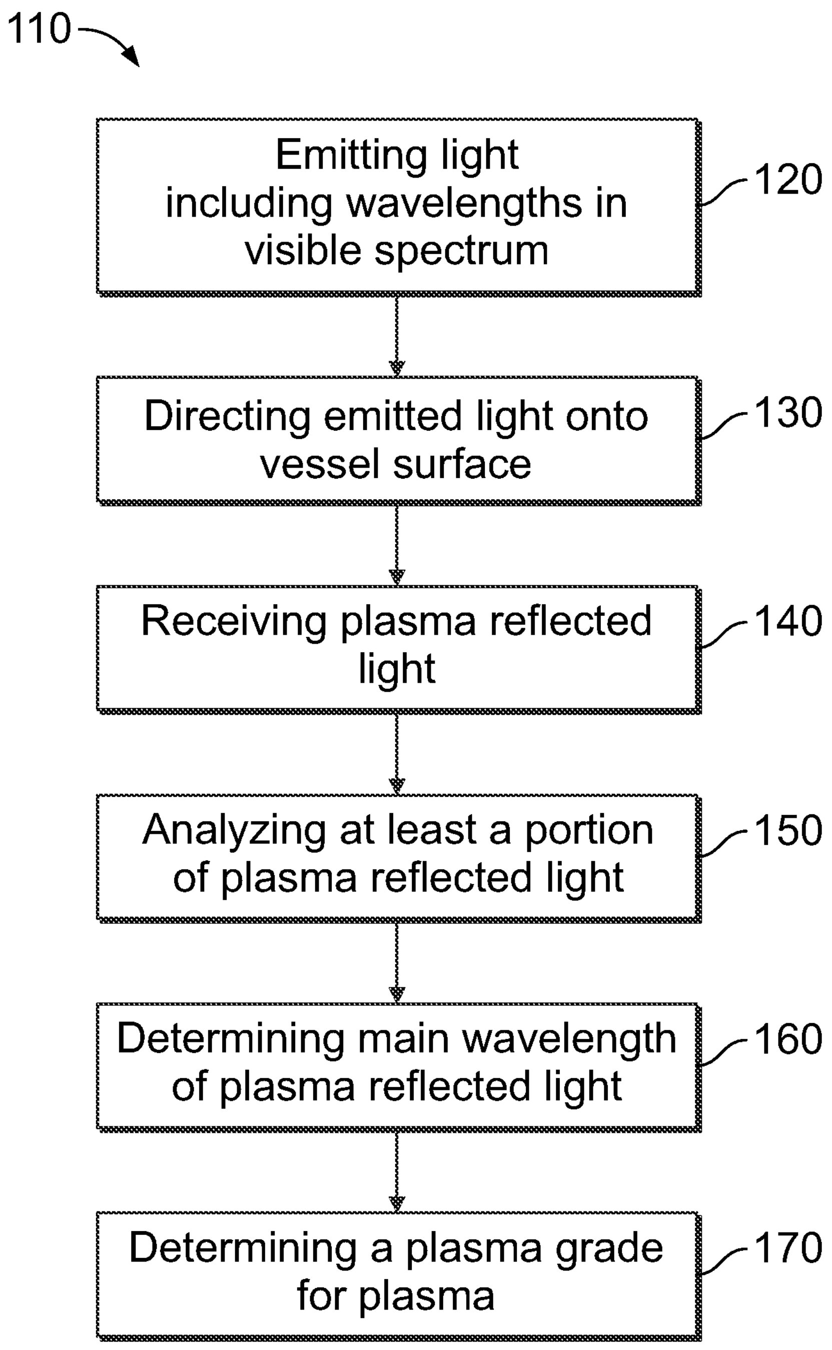
FIG. 9 is block diagram showing an example of a method for determining a plasma grade according to examples of the present disclosure.

Referring now to FIG. 9, a method 110 for grading blood plasma according to embodiments of the present disclosure includes, for example, emitting 120 a light 18 including wavelengths in a visible spectrum and directing 130 the emitted light 18 onto a vessel 20 at the incidence angle θ. A portion 26 of the emitted light may be transmitted through the vessel 20 to plasma 22 contained in the vessel 20, and a further portion 32 of the light 26 may be reflected by the plasma 22. The method 110 also includes receiving 140 at least a portion of the plasma reflected light 32 at an optical spectrometer 14 and analyzing 150 the received plasma reflected light 32 to determine 160 a main wavelength of the received plasma reflected light 32. The method 110 further includes determining 170 a plasma grade for the plasma 22 based on the main wavelength and the plasma grading information 42. That is, the plasma 22 may be graded (i.e., assigned a grade) using the stored plasma grade associated with a stored wavelength or wavelength range which corresponds to the main wavelength.

In some embodiments, directing 130 the emitted light 18 from the broadband light source 12 onto the vessel 20 surface may include directing the light 18 onto the vessel 20 surface with at least one optical transmission fiber 30 of an optical fiber bundle 28. The at least one optical transmission fiber 30 may be oriented to direct the emitted light 18 onto the vessel 20 surface at the predetermined incidence angle θ. In addition, receiving 140 reflected light from the plasma 22, i.e., the plasma reflected light 32, may include receiving the plasma reflected light 32 with at least one optical reception fiber 34 of the optical fiber bundle 28 such that the optical spectrometer 14 receives the plasma reflected light 32 via the at least one optical reception fiber 34. In some examples, the optical reception fiber 34 may be centrally arranged relative to a plurality of optical transmission fibers 30.

Analyzing 150 the received, plasma reflected light 32 may include measuring and differentiating wavelengths of the received, plasma reflected light 32 and producing an optical spectrum of the plasma reflected light 32. Analyzing 150 the received, plasma reflected light 32 may also include determining an intensity of the plasma reflected light 32 at the different wavelengths from the optical spectrum. The main wavelength associated with the plasma 22 may be determined 160 from the optical spectrum.

Determining 170 the plasma grade may include comparing the main wavelength to one or more stored wavelengths or ranges of wavelengths (of the wavelength information 44), each wavelength or range of wavelength being associated with a stored plasma grade (of the grade information 46). The method 110 may further include identifying a stored wavelength or range of wavelengths that corresponds with the main wavelength and determining 170 the plasma grade for the plasma 22 based on the stored plasma grade associated with the identified stored wavelength or wavelength range.

In some examples, the method 110 further includes generating an output indicative of the determined plasma grade for the plasma 22.

Figure 10:
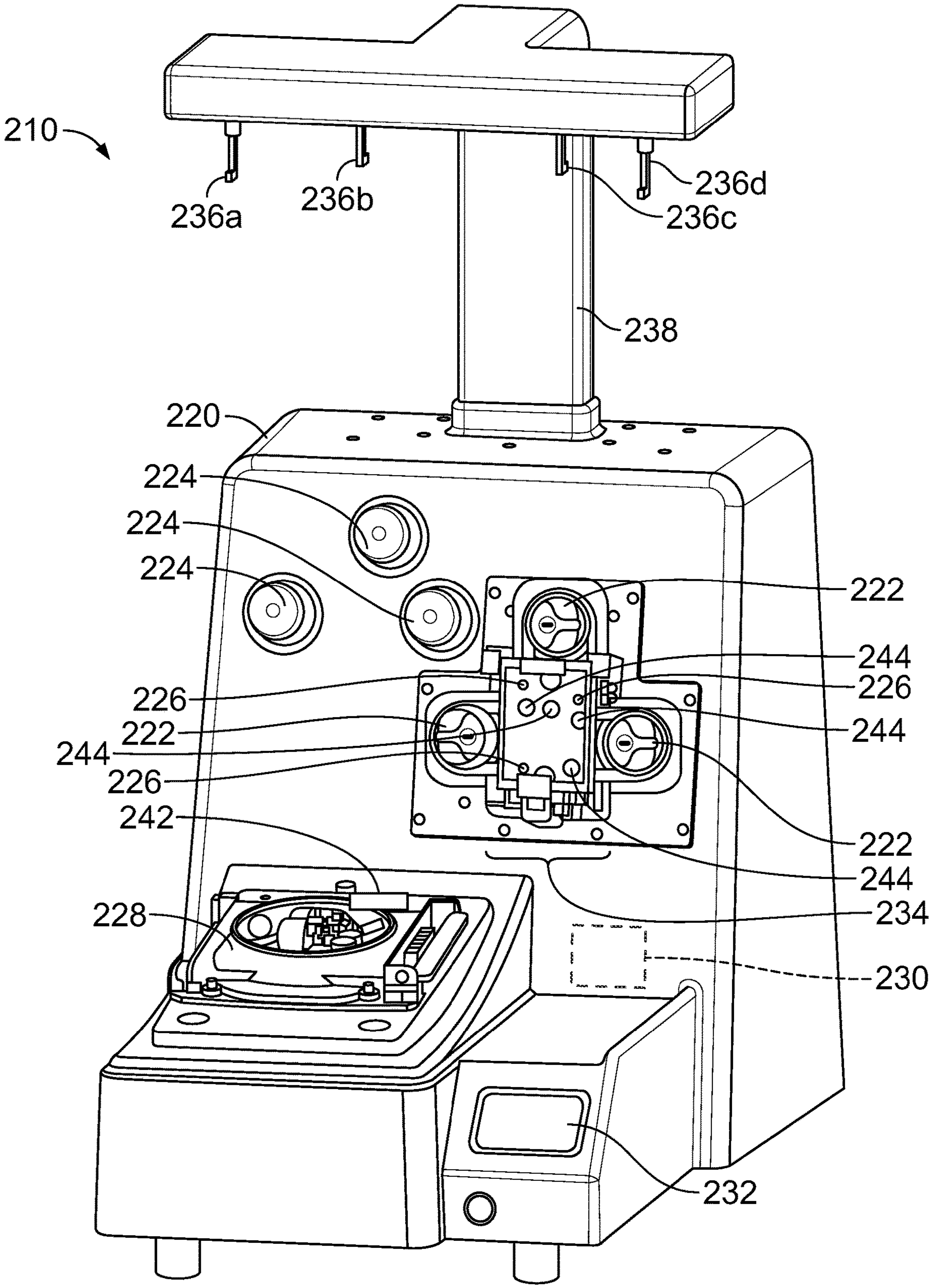
FIG. 10 illustrates an example of a processing device of a blood processing and/or manufacturing system configured for use with the optical plasma grading system of FIG. 1.
Figure 11:
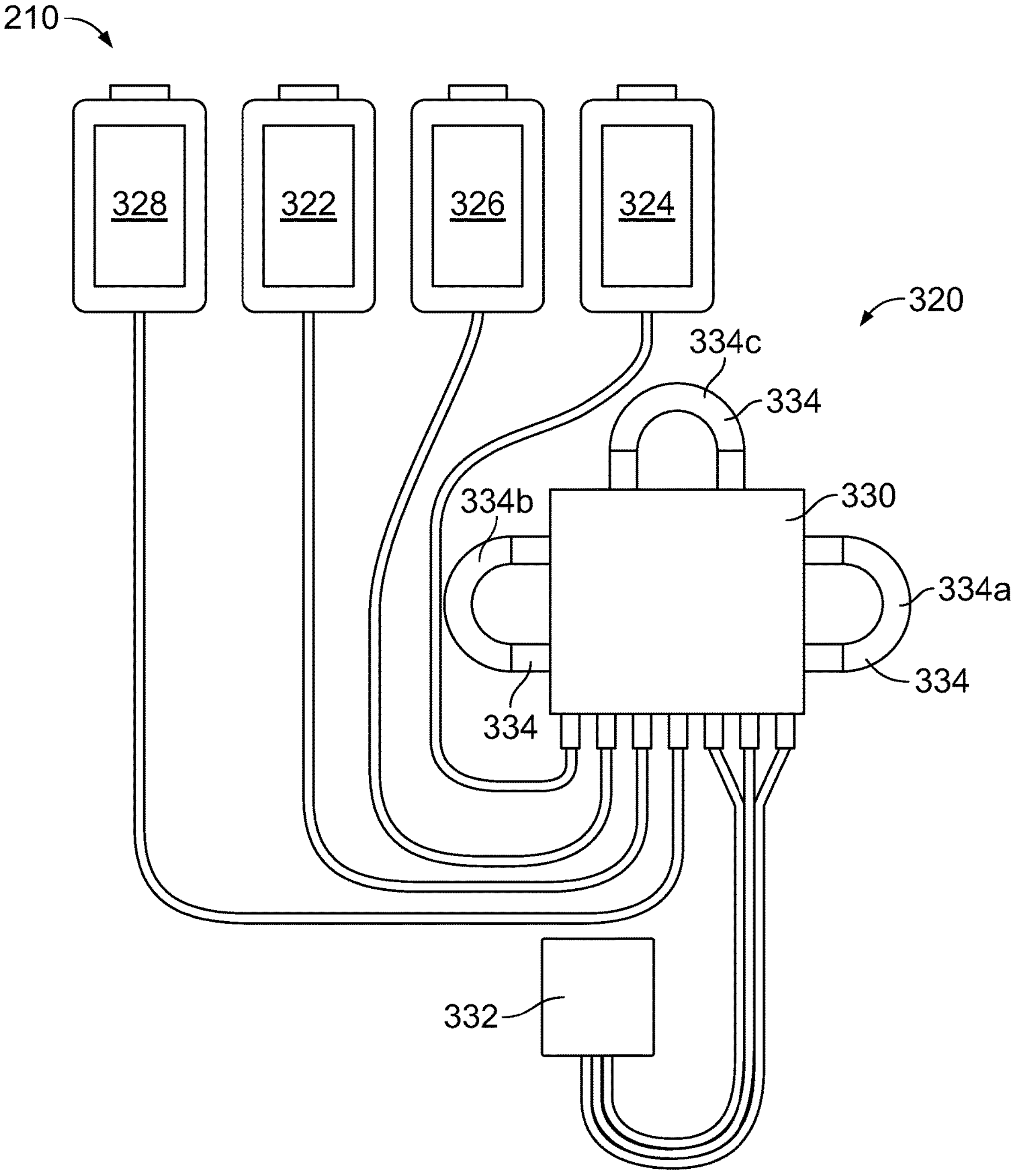
FIG. 11 illustrates an example of a fluid flow circuit of a blood processing and/or manufacturing system configured for use with the optical plasma grading system of FIG. 1 and the processing device of FIG. 11.

The optical plasma grading system 10 of the present embodiments may be used in combination or integrated with a blood processing system and/or a blood component collecting or manufacturing system. With reference to FIGS. 10 and 11, a blood processing or collecting/manufacturing system 210 may generally include a processing device 220 (FIG. 10) and a fluid flow circuit 320 (FIG. 11) selectively usable in combination with the processing device 220. In one example, the processing device 220 includes a pump system 222, a valve system 224, 244, and a centrifuge 228 and centrifuge drive unit (referred to collectively as a "centrifuge"). The processing device 220 may also include a sensor system 226, a microprocessor-based controller 230, and a user interface 232 configured to receive instructions from a user and output information to the user. The user interface 232 may be a touchscreen display. The processing device 220 may further include a nesting module 234 configured to interface with a cassette of the fluid flow circuit 320 as described below. It will be appreciated, that in some examples, the microprocessor-based controller 230 and/or the user interface 232 may be integrated with the controller 16 and/or user interface device 48 described above with respect to the optical plasma grading system 10.

The fluid flow circuit 320 may generally include a plurality of fluid containers, such as a whole blood container 322, a plasma container 324, a red blood cell container 326 and an additive container 328. The fluid flow circuit 320 may also include a flow control cassette 330 configured to be selectively coupled with the nesting module 234 of the processing device 220 and may further include a processing/separation chamber 332 configured to be received in the centrifuge 228. The fluid containers 322, 324, 326, 328, flow control cassette 330 and processing/separation chamber 332 are interconnected to one another by conduits or tubing segments so as to permit continuous flow centrifugation.

The pump system 222 and valve system 224 of the processing device 220 are selectively operable to draw whole blood from the whole blood container 322 or other source and direct the whole blood through a selected flow path for performing a selected blood processing or blood manufacturing process. In one example, as described further below, the pumps 222, valves 224 and sensors 226 of the processing device 220 may be operated to draw whole blood from the whole blood container 322, through a flow path which causes the whole blood to be separated into plasma 22 and red blood cell components. For example, the flow path may direct the whole blood through the centrifuge 228 which may be operated to separate the blood components. The pump system 222 and valve system 224 may be further operated to direct the separated blood components to corresponding fluid containers, e.g., to direct the plasma 22 to the plasma container 324.

Figure 13:
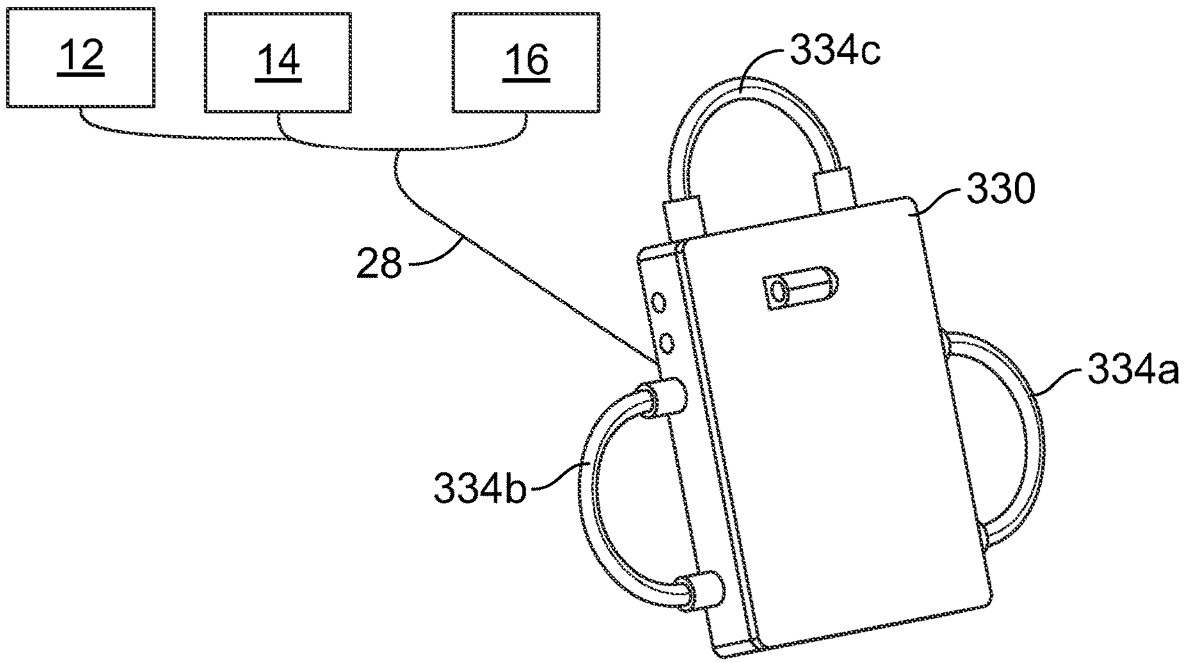
FIG. 13 is a diagram showing an example the optical plasma grading system of FIG. 1 arranged with respect to a flow control cassette of the fluid flow circuit of FIG. 11.

According to one example, as shown in FIGS. 11 and 13, the optical plasma grading system 10 may be configured to grade plasma 22 along the flow path between the centrifuge 228 and the plasma container 324. For example, the broadband light source 12 may be arranged to direct light onto a vessel 20 containing the plasma, such as a fluid conduit through which the plasma 22 flows generally at the flow control cassette 330. In such an example, the fluid conduit may be considered as the vessel 20 described above. Thus, the plasma 22, i.e., the separated plasma 22 flowing from the centrifuge 228 to the plasma container 324, is moving through the fluid conduit while the optical plasma grading system 10 operates to determine a main wavelength of the plasma 22.

Figure 14:
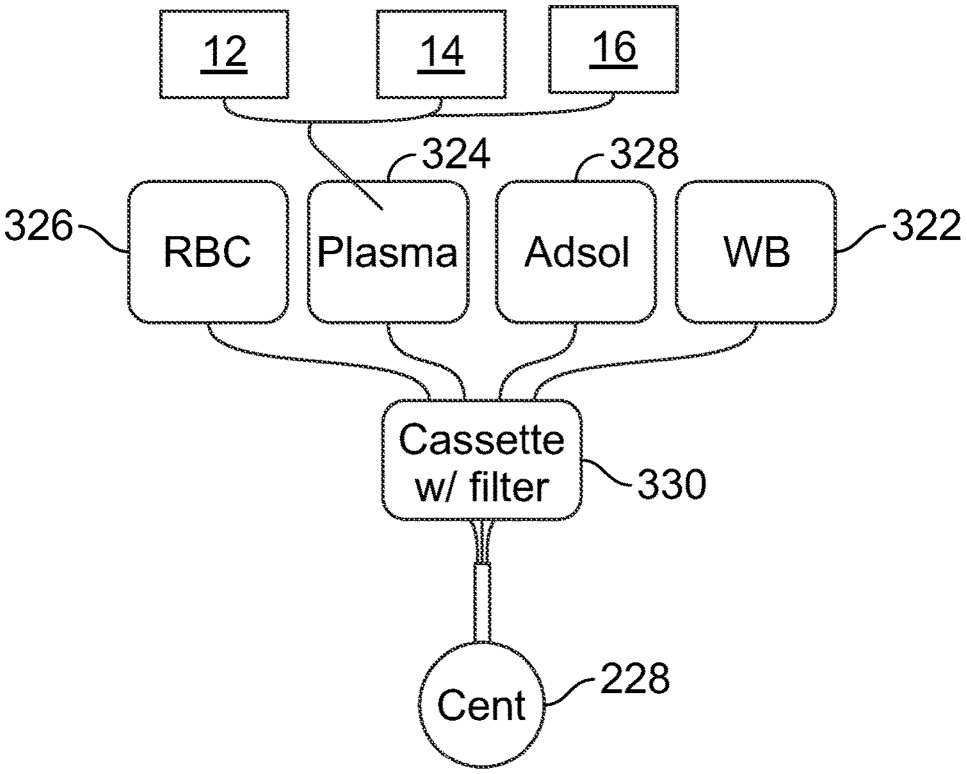
FIG. 14 is a diagram showing an example the optical plasma grading system of FIG. 1 arranged with respect to a fluid container of the fluid flow circuit of FIG. 11.

In another example, as shown in FIGS. 11 and 14, the optical plasma grading system 10 may be configured to grade plasma 22 stored in the plasma container 324. For example, the broadband light source 12 may be arranged to direct light 18 onto the plasma container 324 and receive light reflected from the plasma 22, i.e., the plasma reflected light 32. In such an example, the plasma container 324 may be considered as the vessel 20 described above. Further, in such an example, the plasma 22, i.e., the plasma 22 stored in the plasma container 324, is substantially stationary while the optical plasma grading system 10 operates to determine the main wavelength of the plasma 22.

An example of a blood processing or blood component collecting or manufacturing system 210 of the type described above (without the optical plasma grading system of the present disclosure) is shown and described in WO2021/194824, which is incorporated by reference herein. It will be appreciated, however, that the optical plasma grading system 10 may be used in combination or integrated with differently configured blood processing and/or manufacturing systems.

Figure 12:
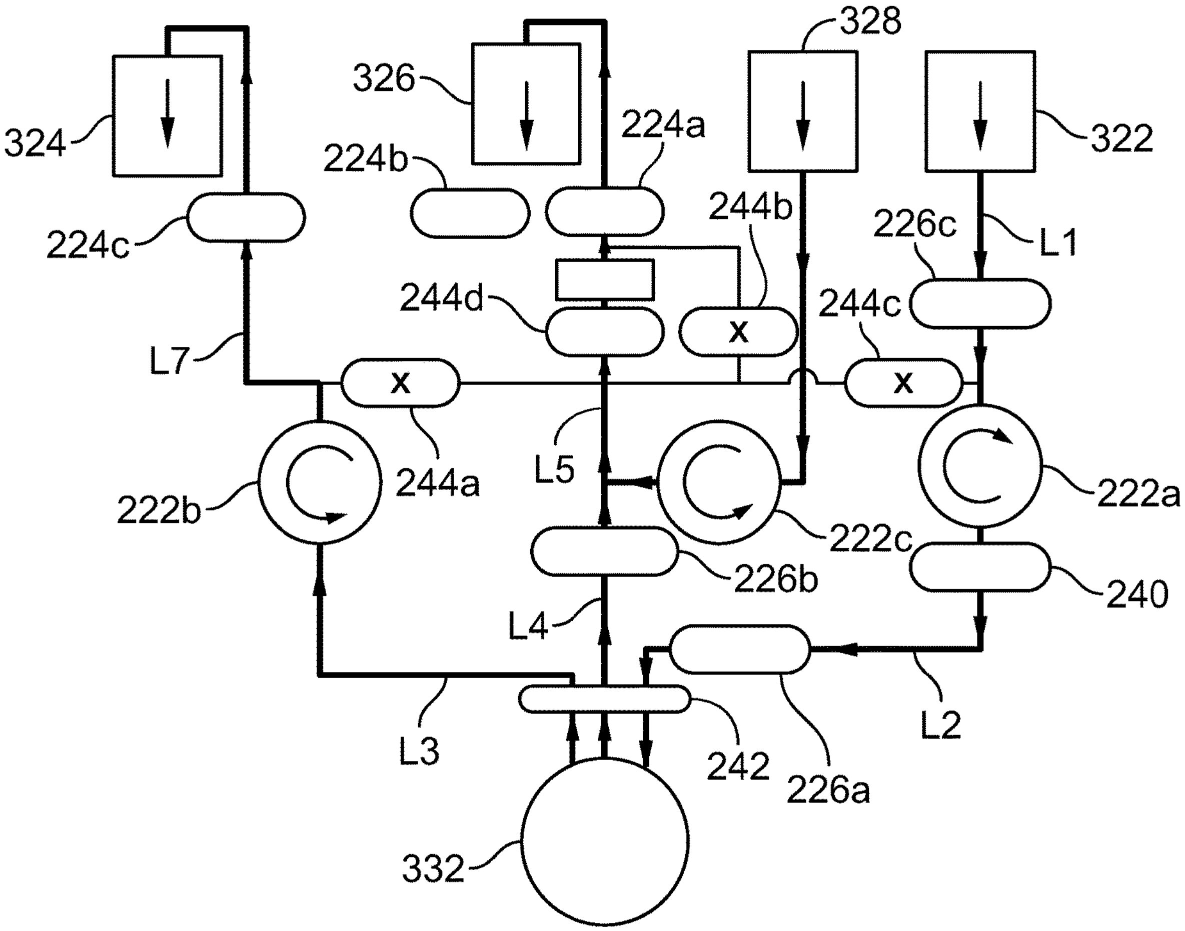
FIG. 12 is a schematic diagram of a plasma flow path through the blood processing and/or manufacturing system of FIGS. 10 and 11.

Referring to FIGS. 10 and 12, the pump system 222 of the processing device 220 may include a first pump 222*a* for pumping whole blood, a second pump 222*b* for pumping plasma 22 and a third pump 222*c* for pumping additive solution. The pumps 222*a-c* may be provided as peristaltic pumps capable of receiving tubing or conduits and moving fluid at various rates through the associated conduit dependent upon the procedure being performed.

The valves 224 include clamps 224*a*, 224*b*, 224*c*. The clamps 224*a-c* are configured to open and close fluid paths through the tubing or conduits and may incorporate RF sealers in order to complete a heat seal of the tubing or conduit placed in the claim to seal the tubing or conduit leading to a fluid container 322, 324, 326, 328 upon completion of a procedure.

As previously indicated, the user interface 232 may be provided as a touchscreen configured to enable user interaction with the processing device 210 and/or monitor various procedure parameters. In one example, the output indicative of the plasma grade may be provided to the touchscreen 232 to inform the user of the plasma grade determined for plasma 22.

Referring to FIGS. 10-12, the flow control cassette 330 is configured to route the fluid flow through three tubing loops 334*a*, 334*b*, 334*c* with each loop being positioned to engage a particular one of the pumps 222*a*, 222*b*, 222*c*. The conduit or tubing may extend through the cassette 330, or the cassette 330 may have preformed fluid flow paths that direct the fluid flow.

The microprocessor-based controller 230 of the processing device 220 may be configured to direct operations the blood processing or manufacturing system 210. The controller 230 may include a programmable microprocessor to automatically control the operation of the pump system 222, the valve system 224, 244 etc. The processing device 220 may also include wireless communication capabilities to enable transfer of data from the processing device 220 to, for example, a quality management system of an operator.

The processing device 220 may also include hangers 236*a-d* configured for supporting (e.g., suspending), various fluid containers 322, 324, 326, 328 of the fluid flow circuit 320. The hangers 236*a-d* may be mounted to a support 238 which is vertically translatable to improve transportability of the processing device 10.

The nesting module 234 is configured to receive various disposable cassette designs so that the system may be used to perform different types of procedures. Embedded within the illustrated cassette nesting module 234 are four valves 244*a-d* (collectively referred to herein as being part of the "valve system 224, 244") for opening and closing fluid flow paths within the flow control cassette 330, and three pressure sensors 226*a-c* capable of measuring the pressure at various locations of the fluid flow circuit 320.

The controller 230 of the processing device 220 is pre-programmed to automatically operate the system to perform one or more standard blood processing procedures selected by an operator input to the touchscreen 232 and configured to be further programmed by the operator to perform additional blood processing procedures. The controller 230 may be pre-programmed to substantially automate a wide variety of procedures carried out by the blood processing or manufacturing system 210, including, but not limited to: red blood cell and plasma production from a single unit of whole blood, buffy coat pooling, buffy coat separation into a platelet product, glycerol addition to red blood cells, red blood cell washing, platelet washing and cryoprecipitate pooling and separation.

The pre-programmed blood processing procedures operate the system 210 at pre-set settings for flow rates and centrifugation forces, and the programmable controller 230 may be further configured to receive input from the operator as to one or more of flow rates and centrifugation forces for the standard blood processing procedure to override the pre-programmed settings.

In addition, the programmable controller 230 is configured to receive input from the operator through the touchscreen 232 for operating the system 210 to perform a non-standard blood processing procedure. More particularly, the programmable controller 230 may be configured to receive input for settings for the non-standard blood processing procedure, including flow rates and centrifugation forces.

The controller 16 of the optical plasma grading system 10 may be separate from the controller 230 of the blood processing and collecting/manufacturing system 210. In some examples, the controllers 16, 230 may be arranged in communication with one another such that information may be transmitted/received between the controllers 16, 230. Alternatively, the controller 16 of the optical plasma grading system 10 and the controller 230 of the blood processing or collecting/manufacturing system 210 may be integrated and provided as a single controller configured to perform the operations detailed above with respect to both controllers.

Although the processing device 220 is configured to perform various blood processing operations as described above, it will be appreciated that the optical plasma grading system 10 of the present embodiments may operate in conjunction with a plasma separation and/or collection process. Accordingly, description of the other blood processing operations which may be performed by the processing device 220 is omitted below.

FIG. 12 is a diagram illustrating the fluid path in the blood processing and/or blood component collecting/manufacturing system 210 when controlled to perform a plasma and red blood cell separation or collection process. That is, FIG. 12 illustrates a flow path resulting from the selective operation of the pump system 222 and the valve system 224, 244, and other processing device components, including the centrifuge 228, to separate whole blood into plasma 22 and red blood cell components and to collect plasma 22 in the plasma container 324 and red blood cells in the red blood cell container 326. Description relating to separation and collection of the red blood cells from the whole blood may be omitted below.

In the example of FIG. 12, to perform the plasma and red blood cell separation process, the whole blood pump 222*a* is operated to draw whole blood from the whole blood container 322 into line L1, valve 244*c* is closed, which directs the blood through pressure sensor 226*c* and into line L2, through air trap 240, pressure sensor 226*a* and optical sensor 242 before flowing into the separation chamber 332, which is positioned within the centrifuge 228. The centrifuge 228 is operated at rate sufficient to separate blood into packed red blood cells and platelet-poor plasma.

At the beginning of a collection stage, the centrifuge 228, the whole blood pump 222*a* and the plasma pump 222*b* all operate and the valves 244 are adjusted to direct the separated plasma and red blood cells to their respective fluid containers 324, 326 while causing additional blood to be drawn into the fluid flow circuit 320 from the blood source, i.e., the whole blood container 322. In particular, the valve 244*c* is closed, which causes the whole blood pump 222*a* to draw additional blood into line L1 from the whole blood container 322, and further, into L2 and passing though air trap 240, pressure sensor 226*a*, and optical sensor 242 before flowing into the separation chamber 332, where it is separated into plasma 22 and red blood cells. The separated plasma 22 exits the separation chamber 332 via the plasma outlet port and associated line L3. Valve 244*a* is closed, which directs plasma 22 from line L3 into line L7, through open clamp 224*c* and into the plasma container 324. The red blood cells may exit the separation chamber 332 via a red blood cell output port to lines L4 and L5.

With reference to FIGS. 12 and 13, in one example, the components of the optical plasma grading system 10 are configured to measure the main wavelength from the plasma fluid path, i.e., a vessel in which plasma flows, are arranged on a backside of the flow control cassette 330 mounted on the nesting module 234. For example, the broadband light source 12 may be arranged and configured to emit light 18 to a portion of the vessel 20 i.e., the flow control cassette 330 and the plasma flow path therein (shown as L3 and L7 in FIG. 12). Similarly, the optical spectrometer 14 may be arranged and configured to receive a portion of the light reflected by the plasma within the plasma flow path (shown as L3 and L7, FIG. 12) of cassette 330.

With reference to FIGS. 12 and 14, in another example, components of the optical plasma grading system 10 configured to measure the main wavelength from plasma 22 are arranged on a backside of the plasma container 324, i.e., a plasma collection bag 324 configured to collect separated plasma 22. For example, the broadband light source 12 may be arranged and configured to emit light 18 to a portion of the vessel 20, i.e., the plasma container 324, and the optical spectrometer 14 may be arranged and configured to receive light reflected from the plasma 22 within the plasma container 324.

In various embodiments, the main wavelength determined by the optical plasma grading system 10 may be stored, for example in a memory 38, as main wavelength information 50. The main wavelength information 50 may include one or more main wavelength values. Alternatively, or in addition, the main wavelength information 50 may include an average of the main wavelengths determined throughout a blood processing or manufacturing procedure performed by the system 210. In further examples, the average main wavelength value may be used to determine the plasma grade for the plasma 22.

Figure 15:
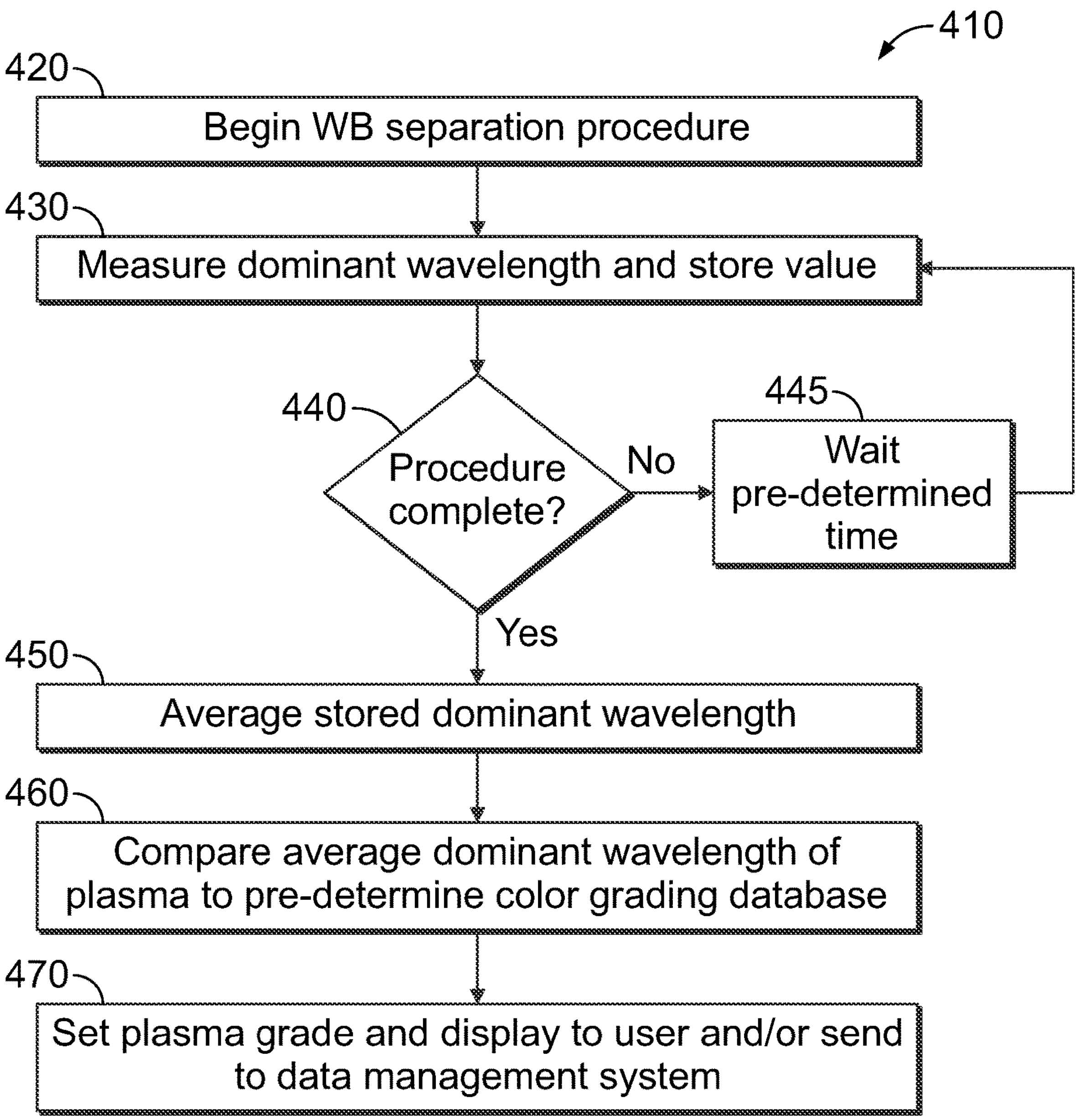
FIG. 15 is a block diagram showing another method for determining a plasma grade according to examples of the present disclosure.

For example, FIG. 15 shows another example of a method 410 for grading plasma in a blood separation process. The method 410 may include, for example, beginning 420 a whole blood separation procedure and measuring 430 a main or dominant wavelength of light by separated plasma 22 during the blood separation procedure. The method 410 includes checking 440 whether the procedure is complete and waiting 445 a predetermined time if the procedure is not complete. After waiting the predetermined time, the method 410 returns to measuring 430 a main or dominant wavelength. If the procedure is complete, the method 410 includes averaging 450 stored main or dominant wavelength values of the plasma 22. The method 410 further includes comparing 460 the average main or dominant wavelength of the plasma 22 to a predetermined color grading database. In one example, the predetermined color grading database may be stored in the memory 38, for example, as the plasma grading information 42. The method 410 may also include setting 470 the plasma grade for plasma 22 according to the average main wavelength and the predetermined color grading database and displaying the plasma grade to the user and/or sending the plasma grade to a data management system.

In one example, a facility's data management system (not shown) may receive the determined plasma grades from the system 10 and/or system 210. The data management system may be configured to determine a final application of the plasma (e.g., fractionation, transfusion, cryoprecipitate, disposal, etc.) based on the determined plasma grade. Alternatively, or in addition, a user of the system 10, 210 may determine the final application of the plasma 22 based on the determined plasma grade.

In the embodiments of the present application, plasma grading may be automated by way of the optical plasma grading system 10 by incorporating color measurement technology, for example, into a blood processing or manufacturing system 210. The embodiments of the present application may allow the system to automatically grade the plasma which can then be displayed to a user/operator and/or sent to a facility's data management system. In this manner labor associated manual plasma grading may be reduced and overall consistency in grading may be improved by removing human subjectivity or error.

Aspects

Aspect 1. A method for grading blood plasma, the method comprising: emitting, from a broadband light source, light having wavelengths in a visible range; directing the emitted light to a vessel at an incidence angle; receiving, at an optical spectrometer, a reflected light portion of the emitted light; analyzing, with the optical spectrometer, at least a portion of the received reflected light to determine a main wavelength of the received reflected light; and determining, with a controller, the plasma grade of the plasma using the main wavelength.

Aspect 2. The method of Aspect 1, wherein directing the emitted light includes: transmitting, with one or more optical transmission fibers of a fiber bundle, the emitted light from the broadband light source to the vessel; and arranging the one or more optical transmission fiber to apply the emitted light to a surface of the vessel at the incidence angle.

Aspect 3. The method of Aspect 1, wherein receiving the reflected light portion includes: receiving, with an optical reception fiber of a fiber bundle, the reflected light portion of the emitted light such that the reflected light portion is received at that optical spectrometer via the optical reception fiber.

Aspect 4. The method of any one of the preceding Aspects, wherein determining the plasma grade includes: comparing the main wavelength to one or more stored wavelengths or wavelength ranges; identifying a stored wavelength or wavelength range to which the main wavelength corresponds; and determining the plasma grade of the plasma based on a stored plasma grade associated with the identified stored wavelength or wavelength range.

Aspect 5. The method of any one of the preceding Aspects, wherein the broadband light source is configured to emit light including at least all wavelengths in the visible range.

Aspect 6. The method of Aspect 2, wherein the plasma is arranged in a vessel and the one or more optical transmission fibers are configured to direct light onto the plasma through the vessel.

Aspect 7. The method of Aspect 6, wherein the one or more optical transmission fibers are arranged to direct the light onto the vessel at an incident angle between 0 degrees and 90 degrees.

Aspect 8. The method of Aspect 7, wherein the one or more optical transmission fibers are arranged to direct the light onto the plasma container at an incident angle between 30 degrees and 60 degrees.

Aspect 9. The method of any one of Aspects 6-8, wherein the one or more optical transmission fibers are arranged to direct the light onto the plasma container at an incident angle of about 45 degrees.

Aspect 10. The method of Aspects 2 and 3, wherein the one or more optical transmission fibers includes a plurality of optical transmission fibers, and the optical reception fiber is centrally arranged with respect to the plurality of optical transmission fibers at least at an end where the light is directed onto the vessel.

Aspect 11. The method of any one of the preceding Aspects, wherein the analyzing at least a portion of the received reflected light includes: producing, with the optical spectrometer, an optical spectrum of the received reflected light to determine an intensity of different wavelengths in the visible range of the received reflected light; and determining the main wavelength based at least in part on the optical spectrum.

Aspect 12. The method of any one of the preceding Aspects, wherein the analyzing the received reflected light to determine the main wavelength includes determining the main wavelength as an average main wavelength.

Aspect 13. The method of any one of the preceding Aspects, further comprising generating an output indicative of the plasma grade corresponding to the main wavelength.

Aspect 14. An optical plasma grading system, the system comprising: a broadband light source configured to emit light having wavelengths in a visible spectrum; an optical spectrometer configured to receive a reflected portion of the emitted light and analyze at least a portion of the received, reflected light to determine a main wavelength of the portion of the received reflected light; and a controller operably connected to the optical spectrometer, the controller configured to determine a plasma grade of the plasma based on the main wavelength of the plasma.

Aspect 15. The system of Aspect 14, further comprising an optical fiber bundle operably connected to the broadband light source, the optical fiber bundle comprising at least one optical transmission fiber configured to transmit emitted light from the broadband light source to the vessel and arranged to apply the emitted light to a surface of the vessel at the incidence angle.

Aspect 16. The system of Aspect 14, further comprising an optical fiber bundle operably connected to the optical spectrometer, the optical fiber bundle comprising at least one optical reception fiber configured to receive the reflected portion of the light such that the optical spectrometer is configured to receive the reflected portion of the light via the optical reception fiber.

Aspect 17. The system of any one of Aspects 14-16, wherein to determine the plasma grade, the controller is configured to: compare the main wavelength to one or more stored wavelengths or wavelength ranges; identify a stored wavelength or wavelength range to which main wavelength corresponds; and determine the plasma grade of the plasma based on a stored plasma grade associated with the identified stored wavelength or wavelength range.

Aspect 18. The system of any one of Aspects 14-17, wherein the controller is further configured to generate an output indicative of the determined plasma grade.

Aspect 19. A blood processing and/or manufacturing system, comprising: a processing device having pump system, a valve system, a centrifuge and a nesting module; a fluid flow circuit having a plurality of fluid containers, a flow control cassette, and a separation chamber interconnected with one another with a plurality of fluid conduits, wherein the flow control cassette is removably connected to the processing device at the nesting module and interfaces with one or more pumps of the pump system and one or more valves of the valve system, wherein the separation chamber is received in the centrifuge, and wherein the pump system, valve system, and centrifuge are selectively operable to provide a flow path through which whole blood flows into the separation chamber, is separated by the centrifuge into plasma and red blood cell components, and the plasma flows to a plasma container of the plurality of fluid containers; a broadband light source configured to emit light having wavelengths in a visible spectrum, wherein the emitted light is directed onto a surface of a fluid vessel of the one or more fluid vessels or onto a surface of the plasma container, wherein at least a portion of the emitted light is transmitted through the fluid vessel or the plasma container, and a portion of the transmitted light is reflected by the plasma within the fluid vessel or the fluid container; an optical spectrometer configured to receive at least a portion the light reflected by the plasma and analyze at least a portion of the received, reflected light to determine a main wavelength of the portion of the received reflected light; and a controller operably connected to the optical spectrometer, the controller configured to determine a plasma grade of the plasma based on the main wavelength of the plasma.

Aspect 20. The system of Aspect 19, wherein the controller is configured to: compare the main wavelength to one or more stored wavelengths or wavelength ranges; identify a stored wavelength or wavelength range to which main wavelength corresponds; and determine the plasma grade of the plasma based on a stored plasma grade associated with the identified stored wavelength or wavelength range.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method for grading blood plasma, the method comprising:
- emitting, from a broadband light source, light having wavelengths in a visible range;
- directing the emitted light to a vessel containing the blood plasma to be graded at an incidence angle, where the emitted light is directed onto the blood plasma through the vessel, and where a portion of the emitted light is reflected;
- receiving, at an optical spectrometer, at least some of the reflected light portion of the emitted light;
- analyzing, with the optical spectrometer, the at least some of the reflected light portion, which was received, to determine a main wavelength of the received reflected light portion as an average main wavelength; and
- determining, with a controller, a plasma grade of the blood plasma using the main wavelength.

2. The method of claim 1, wherein directing the emitted light includes:
- transmitting, with one or more optical transmission fibers of a fiber bundle, the emitted light from the broadband light source to the vessel; and
- arranging the one or more optical transmission fibers to apply the emitted light to a surface of the vessel at the incidence angle.

3. The method of claim 2, wherein the one or more optical transmission fibers are configured to direct light onto the blood plasma through the vessel.

4. The method of claim 3, wherein the one or more optical transmission fibers are arranged to direct the light onto the vessel at an incident angle between 0 degrees and 90 degrees.

5. The method of claim 3, wherein the one or more optical transmission fibers are arranged to direct the light onto the vessel at an incident angle between 30 degrees and 60 degrees.

6. The method of claim 3, wherein the one or more optical transmission fibers are arranged to direct the light onto the vessel at an incident angle of about 45 degrees.

7. The method of claim 1, wherein receiving the at least some of the reflected light portion includes:
- receiving, with an optical reception fiber of a fiber bundle, the at least some of the reflected light portion of the emitted light such that the at least some of the reflected light portion is received at that optical spectrometer via the optical reception fiber.

8. The method of claim 1, wherein determining the plasma grade includes:
- comparing the main wavelength to one or more stored wavelengths or wavelength ranges;
- identifying a stored wavelength or wavelength range to which the main wavelength corresponds; and
- determining the plasma grade of the plasma based on a stored plasma grade associated with the identified stored wavelength or wavelength range.

9. The method of claim 1, wherein the broadband light source is configured to emit light including at least all wavelengths in the visible range.

10. The method of claim 1, wherein the fiber bundle includes a plurality of optical transmission fibers and an optical reception fiber, the optical reception fiber being centrally arranged with respect to the plurality of optical transmission fibers at least at an end where the light is directed onto the vessel.

11. The method of claim 1, wherein the analyzing the at least some of the reflected light portion, which was received, includes:
- producing, with the optical spectrometer, an optical spectrum of the received reflected light portion to determine an intensity of different wavelengths in the visible range of the received reflected light portion; and
- determining the main wavelength based at least in part on the optical spectrum.

12. The method of claim 1, further comprising generating an output indicative of the plasma grade corresponding to the main wavelength.

13. A blood processing and/or manufacturing system, comprising:
- a processing device having pump system, a valve system, a centrifuge and a nesting module;
- a fluid flow circuit having a plurality of fluid containers, a flow control cassette, and a separation chamber interconnected with one another with a plurality of fluid conduits, wherein the flow control cassette is removably connected to the processing device at the nesting module and interfaces with one or more pumps of the pump system and one or more valves of the valve system, wherein the separation chamber is received in the centrifuge, and wherein the pump system, valve system, and centrifuge are selectively operable to provide a flow path through which whole blood flows into the separation chamber, is separated by the centrifuge into plasma and red blood cell components, and the plasma flows to a plasma container of the plurality of fluid containers;
- a broadband light source configured to emit light having wavelengths in a visible spectrum, wherein the emitted light is directed onto a surface of a fluid vessel of one or more fluid vessels or onto a surface of the plasma container, wherein at least a portion of the emitted light is transmitted through the one or more fluid vessels or the plasma container, and a portion of the transmitted light is reflected by the plasma within the fluid vessel or the fluid container;
- an optical spectrometer configured to receive at least a portion of the light reflected by the plasma and analyze at least a portion of the received reflected light to determine a main wavelength of the portion of the received reflected light; and
- a controller operably connected to the optical spectrometer, the controller configured to determine a plasma grade of the plasma based on the main wavelength of the portion of the received reflected light.

14. The system of claim 13, further comprising an optical fiber bundle operably connected to the broadband light source, the optical fiber bundle comprising at least one optical transmission fiber configured to transmit emitted light from the broadband light source to the vessel and arranged to apply the emitted light to a surface of the vessel at an incidence angle.

15. The system of claim 13, further comprising an optical fiber bundle operably connected to the optical spectrometer, the optical fiber bundle comprising at least one optical reception fiber configured to receive the at least some of the reflected light portion of the emitted light such that the optical spectrometer is configured to receive the at least some of the reflected light portion of the emitted light via the optical reception fiber.

16. The system of claim 13, wherein to determine the plasma grade, the controller is configured to:

compare the main wavelength to one or more stored wavelengths or wavelength ranges;

identify a stored wavelength or wavelength range to which main wavelength corresponds; and determine the plasma grade of the blood plasma based on a stored plasma grade associated with the identified stored wavelength or wavelength range.

17. The system of claim 13, wherein the controller is further configured to generate an output indicative of the determined plasma grade.

18. The system of claim 13, wherein the controller is configured to:

compare the main wavelength to one or more stored wavelengths or wavelength ranges;

identify a stored wavelength or wavelength range to which the main wavelength corresponds; and determine the plasma grade of the plasma, based on a stored plasma grade associated with the identified stored wavelength or wavelength range.

* * * * *